US010024839B2

(12) United States Patent
Righettini et al.

(10) Patent No.: US 10,024,839 B2
(45) Date of Patent: Jul. 17, 2018

(54) MEASURING DEVICE FOR MEASURING THE FINENESS AND MATURITY OF COTTON FIBERS

(71) Applicant: MESDAN S.p.A., Puegnago del Garda (IT)

(72) Inventors: Antonio Righettini, Salo (IT); Giuseppe Pace, Roe Volciano (IT)

(73) Assignee: MESDAN S.p.A., Puegnago del Garda (IT)

( * ) Notice: Subject to any disclaimer, the term of this patent is extended or adjusted under 35 U.S.C. 154(b) by 68 days.

(21) Appl. No.: 15/334,672

(22) Filed: Oct. 26, 2016

(65) Prior Publication Data
US 2017/0122924 A1   May 4, 2017

(30) Foreign Application Priority Data
Oct. 30, 2015   (IT) .................. 102015000067620

(51) Int. Cl.
*G01N 33/36* (2006.01)
*G01N 15/08* (2006.01)
(Continued)

(52) U.S. Cl.
CPC .......... *G01N 33/365* (2013.01); *D01G 23/08* (2013.01); *D01G 31/00* (2013.01); *G01N 19/00* (2013.01); *G01N 33/36* (2013.01); *G01L 13/00* (2013.01)

(58) Field of Classification Search
CPC ........ D01G 23/08; D01G 31/00; G01L 13/00; G01N 33/365; G01N 19/00; G01N 33/36;
(Continued)

(56) References Cited

U.S. PATENT DOCUMENTS 3,416,376 A    12/1968   Johnson et al.
4,891,967 A *  1/1990    Vogt ................. D01G 99/00
                                                    73/38
(Continued)

FOREIGN PATENT DOCUMENTS

EP    0 007 373 A1    2/1980
EP    0 311 569 A1    4/1989
(Continued)

OTHER PUBLICATIONS

Italian Search Report dated May 13, 2016 in Italian Application UB20154753, filed Oct. 30, 2015 (with English translation of Categories of Documents).

*Primary Examiner* — David A Rogers
(74) *Attorney, Agent, or Firm* — Oblon, McClelland, Maier & Neustadt, L.L.P.

(57) ABSTRACT

A measuring device for measuring the fineness and maturity of cotton fibers is provided. The measuring device includes a measuring chamber; a supply conduit; a flow regulator arranged along the supply conduit; a first pressure sensor upstream of the flow regulator; a second pressure sensor downstream of the flow regulator; an electronic proportional pressure regulator for regulating the air pressure in the supply conduit; and an electronic processing and control unit programmed to control the electronic proportional pressure regulator as a function of the detections of the first sensor and of the second sensor or of the second sensor alternatively and respectively to keep the difference between the air pressure upstream and downstream of the flow regulator or the air pressure entering the measuring chamber substantially constant and equal to a predeterminable value.

4 Claims, 5 Drawing Sheets

(51) Int. Cl.
*G01N 19/00* (2006.01)
*D01G 23/08* (2006.01)
*D01G 31/00* (2006.01)
*G01L 13/00* (2006.01)

(58) Field of Classification Search
CPC . G01N 21/8915; G01N 15/0826; G01N 22/04
See application file for complete search history.

(56) References Cited

U.S. PATENT DOCUMENTS

| | | | | |
|---|---|---|---|---|
| 5,359,880 A * | 11/1994 | Elam | ................ | G01N 15/08 73/38 |
| 5,537,868 A * | 7/1996 | Shofner | ................ | G01N 33/362 73/160 |
| 5,892,142 A * | 4/1999 | Ghorashi | ................ | G01N 33/362 73/38 |
| 5,934,997 A * | 8/1999 | Nelson | ................ | G01F 1/663 460/149 |
| 6,314,806 B1 * | 11/2001 | Ghorashi | ................ | G01N 33/362 19/66 CC |
| 6,532,798 B1 * | 3/2003 | Shofner | ................ | D01G 31/006 73/38 |
| 6,543,275 B2 * | 4/2003 | Wu | ................ | G01N 15/0826 73/159 |
| 6,691,563 B1 * | 2/2004 | Trabelsi | ................ | G01N 22/04 324/640 |
| 6,698,274 B2 * | 3/2004 | Shofner | ................ | D01G 31/006 73/38 |
| 6,837,122 B2 * | 1/2005 | Herrmann | ................ | D01H 13/32 324/633 |
| 7,330,034 B1 * | 2/2008 | Pelletier | ................ | G01N 22/04 324/634 |
| 8,614,586 B1 * | 12/2013 | Kandala | ................ | G01N 27/048 324/639 |
| 8,629,681 B1 * | 1/2014 | Trabelsi | ................ | G01N 22/04 324/637 |
| 2003/0115935 A1 * | 6/2003 | Shofner | ................ | D01G 31/006 73/38 |
| 2005/0235736 A1 | 10/2005 | Seghers et al. | | |

FOREIGN PATENT DOCUMENTS

| | | |
|---|---|---|
| EP | 0 740 144 A2 | 10/1996 |
| WO | WO 03/098209 A1 | 11/2003 |
| WO | WO 2008/035159 A2 | 3/2008 |

* cited by examiner

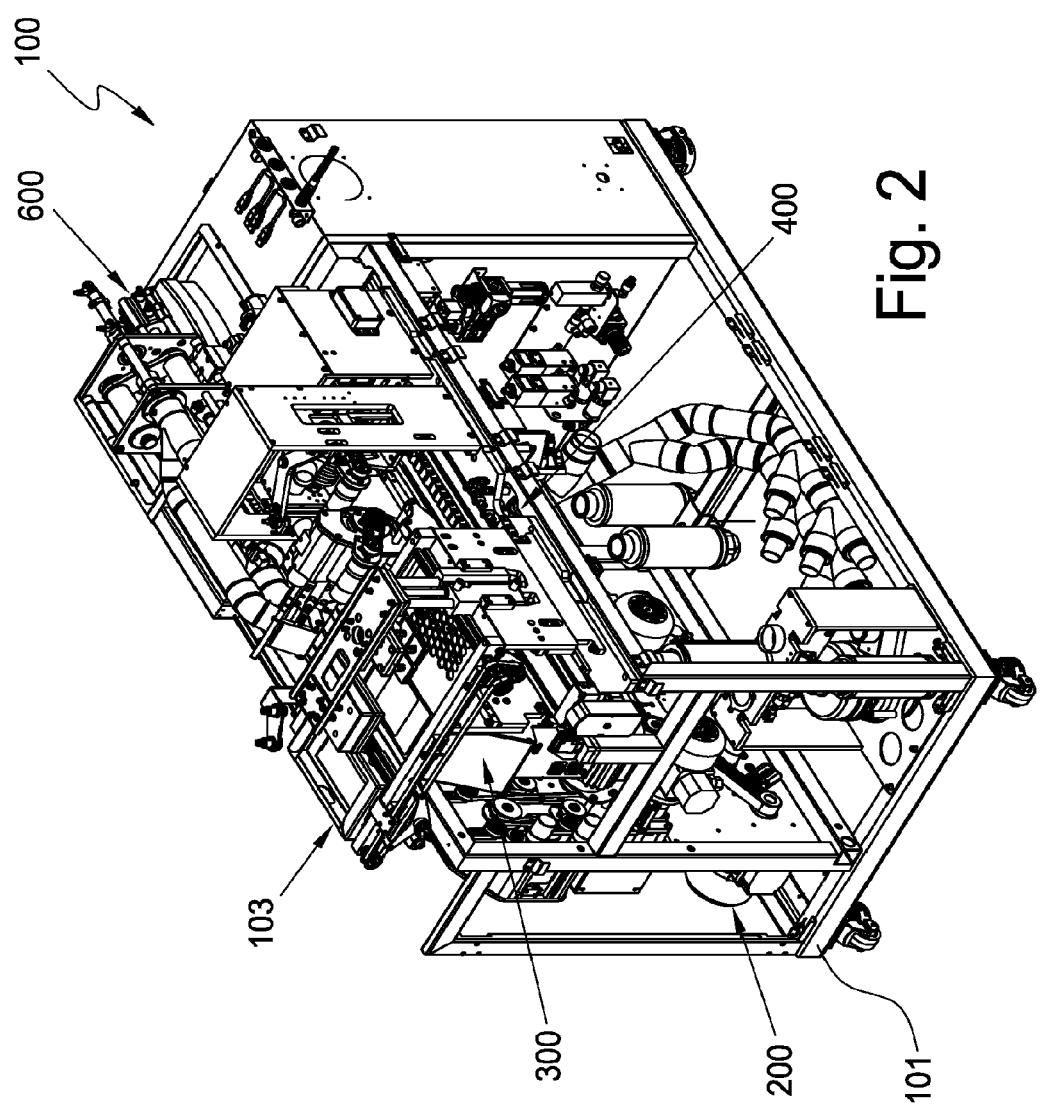

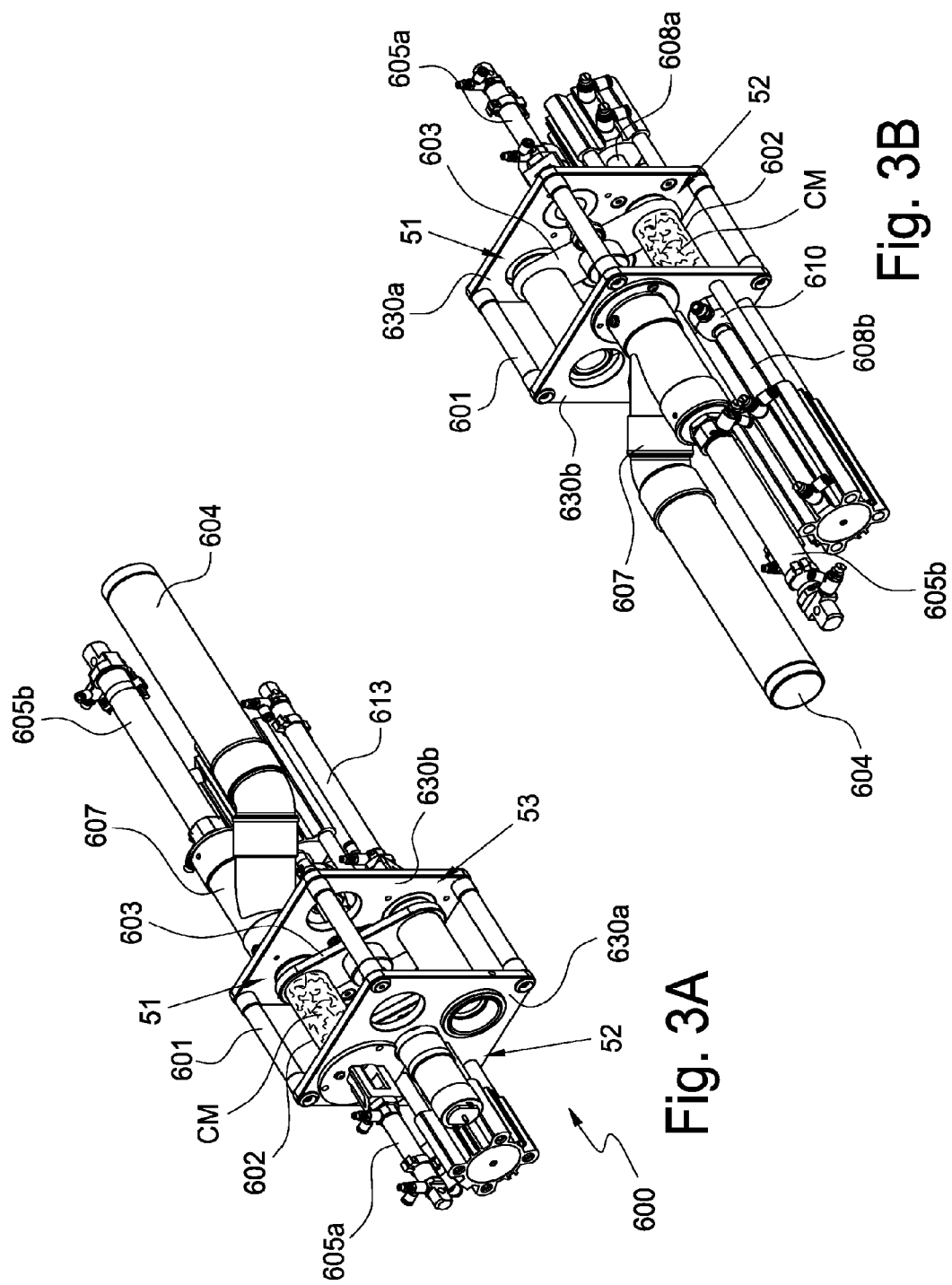

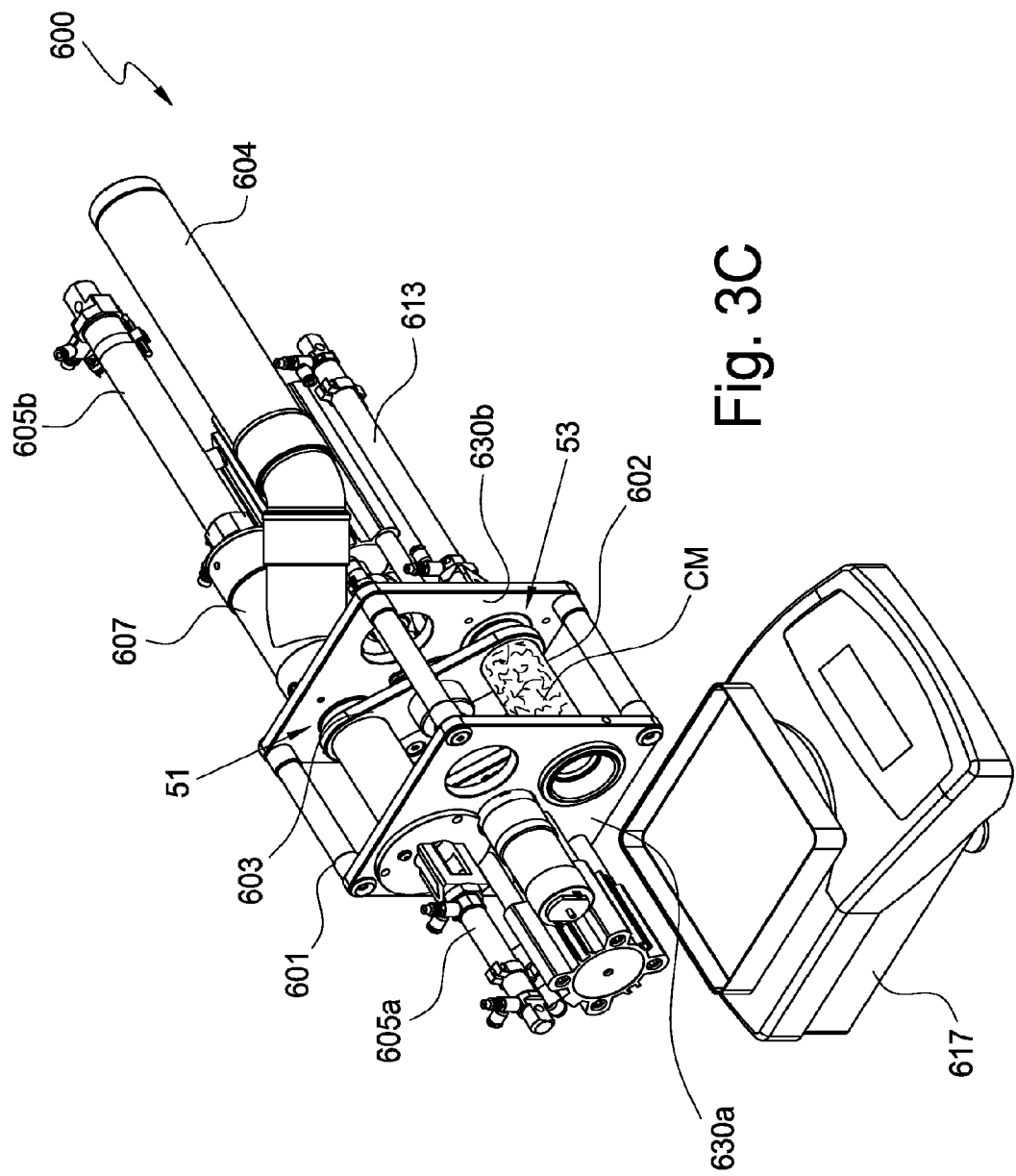

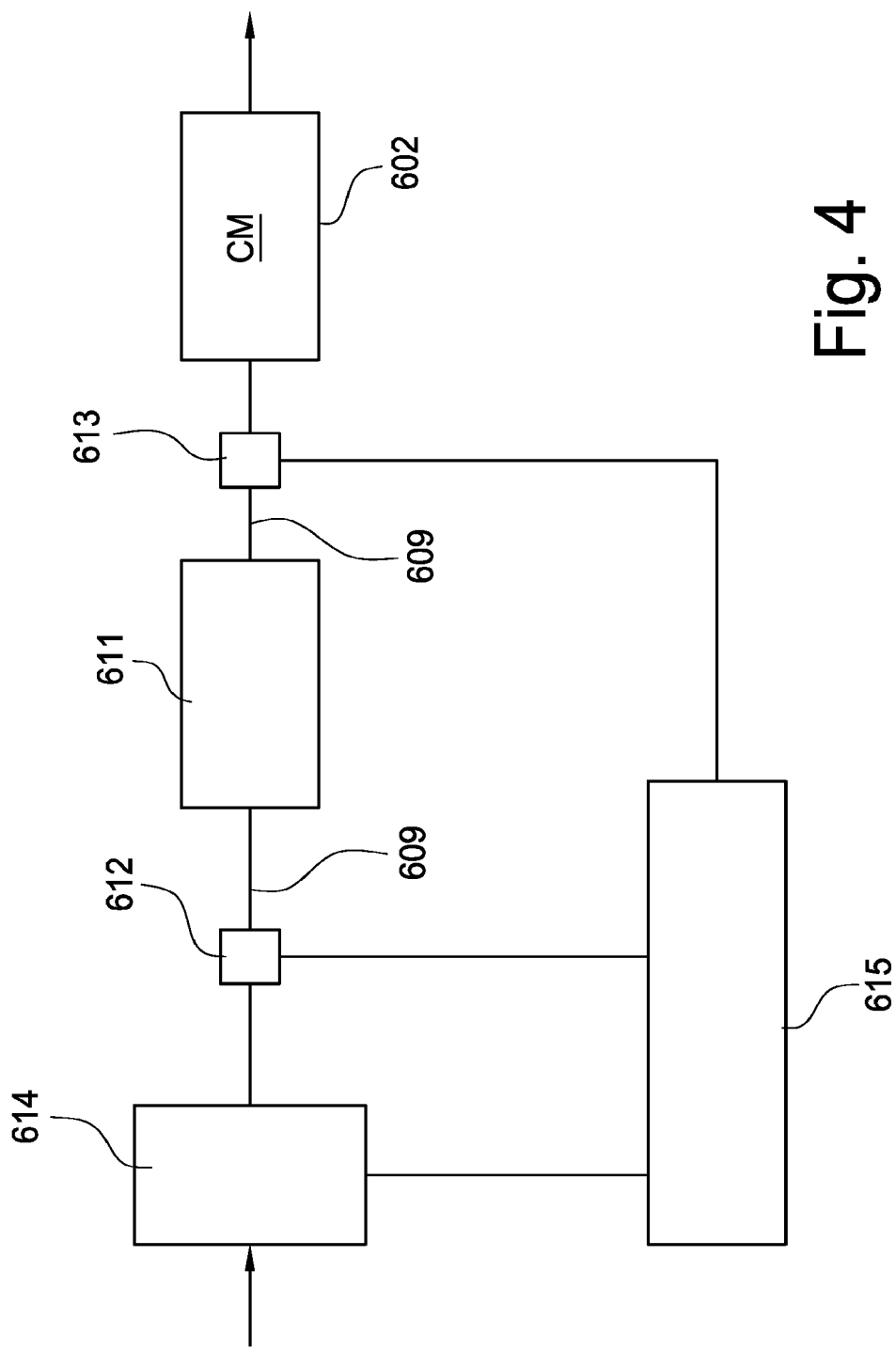

MEASURING DEVICE FOR MEASURING THE FINENESS AND MATURITY OF COTTON FIBERS

The present invention refers to a measuring device for measuring the fineness and maturity of cotton fibers.

Numerous parameters intervene in determining the quality of cotton fibers and, therefore, in their classification according to classifications that are recognized by national or international organizations and that determine, for example, their commercial value, processability or yield.

In general, the quality of cotton fibers is determined by the color, the amount of imperfections, like for example knots or neps of fibers, and of impurities, like for example insect or vegetable residues (seed fragments), by the "cotton stickiness", by the fineness/maturity of the fibers, by the moisture content, by the length and by the dynamometric features (stretching or elongation under tension before breaking and tensile strength, i.e. the maximum load applicable under tension before breaking).

With particular reference to the measurement of the fineness and maturity of cotton fibers, it should be remembered that, as known, mature cotton fibers have a hollow cross section and are in the form of a flattened floss, the inside of which consists of a solid part (cell wall) of cellulose that delimits a hollow part (lumen). Generally, the measurement of the fineness/maturity of cotton fibers obtained with air flow methods is accompanied by the so-called combined fineness and maturity index known in the field as Micronaire.

Devices for measuring the fineness and maturity of cotton fibers are known, which operate with air flow methods, wherein a known quantity of fibers is enclosed in a measuring chamber of known dimensions and crossed by an air flow, the fineness and the maturity of the fibers being determined indirectly from the losses of pressure at the ends of the measuring chamber due to the resistance that the fibers oppose to the air flow that passes through the measuring chamber itself. In these known devices the air flow is supplied to enter the measuring chamber through a supply conduit along which a flow regulator is arranged. Since the resistance to the passage of air of the flow regulator is much higher than that offered by the sample of fibers inserted in the measuring chamber, in general the device is presumed to operate under constant flow conditions. However, this condition of constant flow is not guaranteed, the air flow being able to vary during the course of the tests as the samples tested or the air supply conditions vary. This, therefore, inevitably reflects on the fineness and maturity measurements detected.

The purpose of the present invention is to avoid the drawbacks of the prior art.

In this general purpose, a particular purpose of the present invention is to provide a measuring device for measuring the fineness and maturity of cotton fibers that allows obtaining precise fineness and maturity values under the conditions provided by the current standards.

Another purpose of the present invention is to provide a measuring device for measuring the fineness and maturity of cotton fibers, which is functional and can be used as an independent apparatus or integrated as a module in a modular apparatus for measuring a plurality of features of textile fibers.

The object of the present invention is a measuring device for measuring the fineness and maturity of cotton fibers, as outlined in independent claim no. 1.

Further features are specified in the dependent claims.

The features and advantages of a measuring device for measuring the fineness and maturity of cotton fibers, according to the present invention will become clearer from the following description, given as an example and not for limiting purposes, referring to the attached schematic drawings, in which:

FIGS. 1 and 2 are axonometric views of a modular apparatus for measuring features of cotton fibers, in which one of the measuring modules consists of the measuring device according to the present invention;

FIGS. 3A to 3C show axonometric views of a measuring device for measuring fineness and maturity according to the present invention in successive operating positions;

FIG. 4 is a scheme of the control system of the measuring device for measuring the fineness and maturity of cotton fibers.

Figure 1:
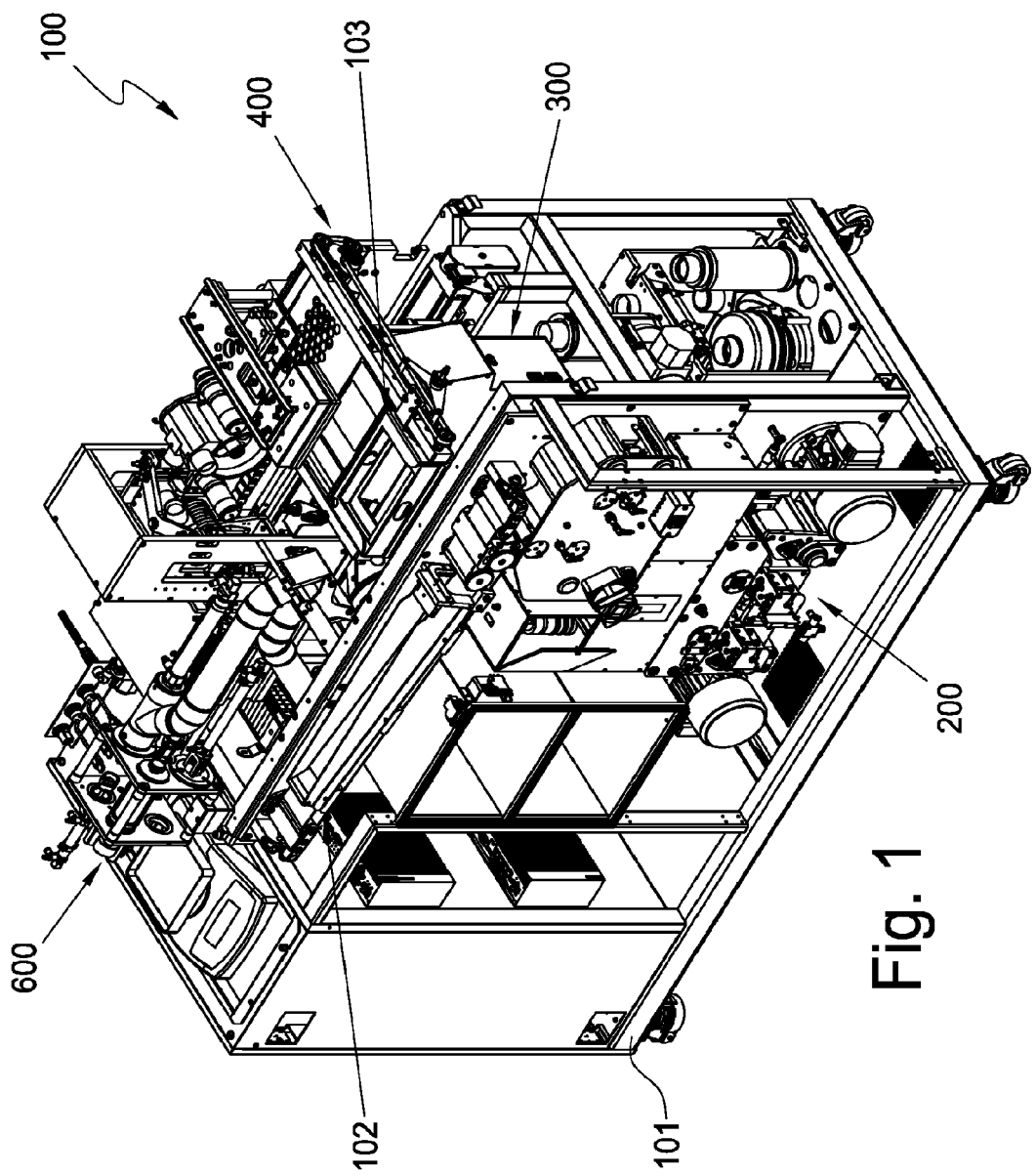

With reference to the figures, a modular apparatus for measuring a plurality of features of cotton fibers has been wholly indicated with 100.

The apparatus 100 comprises a support structure 101 that supports a plurality of modules each comprising at least one measuring device for measuring at least one feature of cotton fibers and a central electronic processing and control unit for controlling and operating such modules and that is not shown since it is of the type known to the person skilled in the art. It is specified that each module constituting the apparatus 100 can be equipped with an own local electronic processing and control unit, which is in turn connected to the central electronic processing and control unit.

In the embodiment represented in the attached figures, the apparatus 100 comprises:

- a first module comprising a measuring device 200 for measuring cotton stickiness and imperfections, of the neps type, and/or impurities, of the seed fragments type, insect or artificial fibers residues, and in particular polymeric or other, present in the cotton fibers,
- a second module comprising a measuring device 300 for measuring the color and detecting impurities of the cotton fibers,
- a third module comprising a measuring device 400 for measuring the moisture content, the length and/or at least one dynamometric feature selected from the group comprising elongation (i.e. the elongation undergone by the fibers before breaking under tension) and strength (i.e. the maximum stress applied to the fibers before breaking) under tension,
- a fourth module comprising a measuring device 600 for measuring the fineness and maturity of the cotton fibers according to the present invention.

The apparatus 100 is provided with two inlet devices for inletting a respective sample of fibers to be tested:

- a first inlet device 102, of the conveyor belt type, for inletting a first sample and that feeds the measuring device 200 for measuring the stickiness and imperfections and/or impurities, and
- a second inlet device 103, of the movable drawer type, for inletting a second sample and that feeds in succession the measuring device 300 for measuring the color and detecting impurities and the measuring device 400 for measuring the moisture content, the length and/or the dynamometric features of the fibers.

The measuring device 600 for measuring the fineness and maturity of fibers is fed by a pneumatic system that picks up the fibers exiting from the measuring device 200 for measuring stickiness, imperfections and/or impurities and conveys them to enter the measuring device 600.

With reference to FIGS. 3A-3C and 4 the measuring device 600 device for measuring the fineness and maturity of cotton fibers that operates according to known air flow methods is now described.

As known, mature cotton fibers have a hollow cross section and are in the form of a flattened floss, the inside of which consists of a solid part (cell wall) of cellulose that delimits a hollow part (lumen). Generally, the measurement of the fineness/maturity of cotton fibers obtained with air flow methods is accompanied by the so-called combined fineness and maturity index known in the field as Micronaire.

As stated above, the measuring device 600 operates with an air flow method, in which a known quantity of fibers is enclosed within a measuring chamber of known dimensions and crossed by an air flow, the fineness and maturity of the fibers being determined indirectly by the losses of pressure at the ends of the measuring chamber due to the resistance that the fibers oppose to the air flow that passes through the measuring chamber itself. Such a measuring device 600 can operate at constant pressure or at constant flow.

The measuring device 600 comprises a support frame 601 on which a measuring chamber CM is mounted, the latter being formed by a hollow cylinder 602, the axially opposite ends of which are open. The hollow cylinder 602 is mounted on the frame 601 in a movable manner between an insertion station S1 at which a known sample of fibers is inserted in the measuring chamber CM, a measuring station S2 at which the measurements are carried out on the sample inserted in the measuring chamber CM and an extraction station S3 at which, at the end of the measurements, the sample of fibers is extracted from the measuring chamber CM. In the embodiment represented in the attached figures, the hollow cylinder 602 is mounted on a carousel 603 that is rotatable about a rotation axis, the insertion station S1, the measuring station S2 and the extraction station S3 being defined along the circular path made by the hollow cylinder 602. The carousel 603 is mounted between a pair of plates 630*a* and 630*b* facing one another and parallel to one another and that are crossed by a plurality of openings, which are adapted to be put in communication with the open ends of the hollow cylinder 602 and at which the three operating stations S1, S2 and S3 are defined.

The insertion station S1 comprises a supply conduit 604 for feeding the cotton fibers entering the hollow cylinder 602, these cotton fibers are sucked from the outlet of the measuring device 200 for measuring the stickiness and can be weighed in advance. The insertion station S1 also comprises a pair of first pistons that are aligned to and opposite one another and can be inserted into the opposite ends of the hollow cylinder 602. These first pistons are actuated by a respective first linear actuator 605*a*, 605*b* between a position extended in the hollow cylinder 602 to compact the sample of fibers inserted in it and a retracted position outside the hollow cylinder 602.

The supply conduit 604 and one of the two first pistons communicate with a same open end of the hollow cylinder 602 by means of a fitting 607 fixed to the frame 601.

The measuring station S2 comprises a pair of second pistons aligned to and opposite one another and insertable into the opposite ends of the hollow cylinder 602 to respectively form a first base and a second base. These second pistons and, consequently, the first base and the second base formed by them, are of the air permeable type; for example, they can be of the type perforated with calibrated holes. The second pistons are actuated by a respective second linear actuator 608A and 608B between at least one position extended in the hollow cylinder 602 and a retracted position outside the hollow cylinder 602. A supply conduit 609 (just schematized in FIG. 11) feeds an air flow entering the hollow cylinder 602 by means of the second piston that defines the first base. The air flow fed to enter the hollow cylinder 602 comes out of it through its second base that communicates with the external environment at ambient pressure.

The supply conduit 609 has an inlet end associable with an air flow source (not shown) and an outlet end associated with a mouth 610 with which the second piston that defines the first base of the hollow cylinder 602 is associated.

Along the supply conduit 609 a flow regulator 611 is arranged, which is interposed between the inlet end and the outlet end of the supply conduit 609 itself. The flow regulator 611 is formed for example by a known throttle valve.

Along the supply conduit 609 two pressure sensors are also arranged: a first pressure sensor 612 for detecting the air pressure that is arranged upstream of the flow regulator 611 and a second pressure sensor 613 for detecting the air pressure that is arranged downstream of the flow regulator 611 and upstream of the first base of the measuring chamber CM.

Advantageously, moreover, an electronic proportional pressure regulator 614 is arranged along the supply conduit 609 upstream of the first pressure sensor 612 for regulating the air pressure in the supply conduit 609.

The first pressure sensor 612, the second pressure sensor 613 and the electronic proportional pressure regulator 614 are connected to an electronic processing and control unit 615 that is programmed to control the electronic proportional pressure regulator 614 as a function of the detections of the first pressure sensor 612 and of the second pressure sensor 613 or of the second pressure sensor 613 alternatively and respectively to keep the difference between the air pressure upstream and downstream of the flow regulator 611 or the air pressure entering the measuring chamber CM substantially constant and equal to a predeterminable value. It is thus possible to operate under substantially constant flow or pressure conditions at the ends of the measuring chamber CM as required by the ASTM D1448-11 standards for carrying out measurements of fineness and maturity and from these of the Micronaire index.

Namely the electronic proportional pressure regulator 614 is selectively and alternatively controlled by the unit 615 in order to keep the pressure difference upstream and downstream of the flow regulator 611 substantially constant and equal to a predetermined value, so as to operate with a substantially constant flow.

Otherwise, the electronic proportional pressure regulator 614 is selectively and alternatively controlled by the unit 615 in order to keep the pressure at the ends of the measuring chamber CM and, therefore, the pressure entering it substantially constant and equal to a predetermined value.

It is thus possible to operate in actual conditions of constant air flow or of constant pressure at the ends of the measuring chamber CM and equal to a predetermined value.

Indeed, it is specified that at the measuring station S2, the second base of the hollow cylinder 602 communicates with the external environment, so that the detections of the second pressure sensor 613 are relative to the atmospheric pressure and provide a measurement of the pressure at the ends of the measuring chamber CM.

The extraction station S3 comprises a third piston that can be inserted in one of the two opposite ends of the hollow cylinder 602. The third piston is actuated by a respective third linear actuator 616 that is movable between a retracted position outside the hollow cylinder 602 and a position extended inside the hollow cylinder 602 in order to push the fibers contained in it so as to exit from the opposite open end thereof. This makes the extraction of the fibers from the measuring chamber CM particularly simple.

The fibers expelled from the hollow cylinder 602 fall onto a scale 617 that detects their weight.

The operation of the measuring device 600 can be immediately understood by the person skilled in the art from the above description and from the attached figures.

In brief, the carousel 603 takes the hollow cylinder 602 at the insertion station S1 where it is filled with a known quantity of fibers, which are compacted by means of the first pistons.

The carousel 603 takes the hollow cylinder 602 thus filled at the measuring station S2, at which the measurements of the pressure drop at the ends of the measuring chamber CM crossed by an air flow are carried out according to known protocols. These measurements, which can be repeated on the same sample under different compacting conditions, can be carried out under conditions of substantially constant flow or of substantially constant pressure.

The carousel 603 then takes the hollow cylinder 602 at the extraction station S3, at which the sample is pushed out of the hollow cylinder 602 by means of the pushing action exerted on it by the third piston. The sample falls onto the plate of the scale 617 and is weighed.

The measurements carried out are then processed with known algorithms for determining the fineness, maturity and from these the Micronaire index.

The remaining devices that constitute the apparatus 100 are not described in detail since they are not part of the present invention, and some of such devices are the object of simultaneous patent applications to the same applicant.

The measuring device for measuring the fineness and maturity of cotton fibers thus conceived can undergo numerous modifications and variants, all of which are covered by the invention; moreover, all of the details can be replaced by technically equivalent elements. In practice, the materials used, as well as the sizes, can be whatever according to the technical needs.

The invention claimed is:

1. A measuring device for measuring the fineness and maturity of cotton fibers comprising:
    a measuring chamber into which a sample of cotton fibers can be inserted, said measuring chamber comprises a first base and a second base that are opposite each other and that can be crossed by an air flow entering said measuring chamber through said first base and exiting from said measuring chamber through said second base,
    a supply conduit having an inlet end associable with an air flow source and an outlet end associated with said first base,
    a flow regulator arranged along said supply conduit between said inlet and outlet ends thereof,
    a first pressure sensor to detect air pressure that is arranged along said supply conduit upstream of said flow regulator,
    a second pressure sensor to detect air pressure that is arranged along said supply conduit downstream of said flow regulator and upstream of said first base of said measuring chamber,
    an electronic proportional pressure regulator arranged along said supply conduit upstream of said first pressure sensor to regulate air pressure inside said supply conduit,
    an electronic processing and control unit associated with said first sensor, with said second sensor and with said electronic proportional pressure regulator and that is programmed to control said electronic proportional pressure regulator as a function of the detections of said first sensor and of said second sensor or of said second sensor alternatively and respectively to keep the difference between the air pressure upstream and downstream of said flow regulator or air pressure entering said measuring chamber substantially constant and equal to a predeterminable value.

2. The measuring device according to claim 1, characterized in that said measuring chamber is defined by an inner volume of a hollow cylinder axially opposite ends of which are open and in that it comprises a pair of air permeable pistons insertable into a corresponding axially opposite end of said hollow cylinder and movable between at least one position extended inside said hollow cylinder and an extracted position outside said hollow cylinder, said pistons defining said first base and said second base.

3. The measuring device according to claim 2, characterized in that said hollow cylinder is associated with a supporting frame in a movable manner at least between a measuring station and an extraction station of the sample of fibers present therein, wherein said extraction station comprises a piston insertable into said hollow cylinder through one of its two axially opposite ends and that is actuated by respective actuator means in a movable manner between the extracted position outside said hollow cylinder and an extended position inside said hollow cylinder to push the sample of fibers present therein exiting from the other one of said axially opposite ends thereof.

4. A modular apparatus for measuring a plurality of characteristics of textile fibers, in particular cotton fibers, said apparatus comprising a plurality of modules each comprising at least one measuring device for measuring at least one characteristic of said textile fibers and a central processing and control unit for controlling said modules, characterized in that one of said modules comprises the measuring device according to claim 1.

* * * * *